United States Patent
Ross, III et al.

(10) Patent No.: US 6,835,939 B2
(45) Date of Patent: Dec. 28, 2004

(54) MISSING LENS DETECTION SYSTEM AND METHOD

(76) Inventors: Denwood F. Ross, III, 1401 Starlight Ct., Jacksonville, FL (US) 32259; Timothy P. Newton, 7622 Sunwood Dr., Jacksonville, FL (US) 32256; James A. Ebel, 8220 Rock Hill La., Jacksonville, FL (US) 32256; Peyman Dehkordi, 9709 Timber Oaks Ct., Knoxville, TN (US) 37922; Robert Lee Simmons, 1763 Shadowood La., Jacksonville, FL (US) 32207; Michael Francis Widman, 2864 Claire La., Jacksonville, FL (US) 32223; Chandra Tan, 3500 Sutherland Ave., Apt. B205, Knoxville, TN (US) 37919

( * ) Notice: Subject to any disclaimer, the term of this patent is extended or adjusted under 35 U.S.C. 154(b) by 11 days.

(21) Appl. No.: 10/372,463

(22) Filed: Feb. 24, 2003

(65) Prior Publication Data

US 2003/0141458 A1 Jul. 31, 2003

Related U.S. Application Data

(60) Division of application No. 09/420,569, filed on Oct. 19, 1999, now Pat. No. 6,548,818, which is a continuation-in-part of application No. 09/187,579, filed on Nov. 5, 1998, now Pat. No. 6,246,062.

(51) Int. Cl.[7] ............................................. G01N 21/64

(52) U.S. Cl. ............................. 250/458.1; 250/461.1; 356/239.6

(58) Field of Search ..................... 250/458.1, 461.1, 250/341.8; 53/57, 58, 73, 74, 498; 294/1.2; 356/239.2, 239.6, 432

(56) References Cited

U.S. PATENT DOCUMENTS

| | | | |
|---|---|---|---|
| 3,666,885 A | 5/1972 | Hemsley et al. | |
| 3,692,985 A | 9/1972 | Kalman | |
| 3,770,969 A | 11/1973 | Ansevin et al. | |
| 3,820,899 A | 6/1974 | McCormack | |
| 3,904,294 A | 9/1975 | Gold et al. | |
| 3,942,900 A | 3/1976 | Garris | |
| 3,988,068 A | 10/1976 | Sprague | |
| 4,002,823 A | 1/1977 | Van Oosterhout | |
| 4,158,502 A | 6/1979 | Greiner et al. | |
| 4,162,126 A | 7/1979 | Nakagawa et al. | |
| 4,317,613 A | 3/1982 | Grosser | |
| 4,390,676 A | 6/1983 | Loshaek | |
| 4,519,041 A | 5/1985 | Fant et al. | |
| 4,528,311 A | 7/1985 | Beard et al. | ................... 524/91 |
| 4,553,847 A | 11/1985 | Lang | |

(List continued on next page.)

FOREIGN PATENT DOCUMENTS

| | | |
|---|---|---|
| DE | 0 063 761 A1 | 11/1982 |
| DE | 3 432 002 | 8/1984 |
| DE | 36 21 092 | 1/1988 |
| DE | 0 491 663 A1 | 6/1992 |
| EP | 0 070 252 A1 | 1/1983 |
| EP | 0686898 A2 | 12/1995 |
| FR | 2 433 767 | 7/1979 |
| GB | 2 014 725 A | 8/1979 |
| GB | 2 171 812 B | 9/1986 |
| JP | 59 160734 A | 9/1984 |
| WO | WO 0016072 | 3/2000 |
| WO | WO 00/46582 | 8/2000 |

*Primary Examiner*—Constantine Hannaher
*Assistant Examiner*—Timothy Moran

(57) ABSTRACT

A system for determining the presence and optionally the position of an ophthalmic product such as a contact lens in a container is provided.

17 Claims, 8 Drawing Sheets

U.S. PATENT DOCUMENTS

| | | |
|---|---|---|
| 4,691,231 A | 9/1987 | Fitzmorris et al. |
| 4,733,360 A | 3/1988 | Kobayashi et al. |
| 4,815,844 A | 3/1989 | Schmalfuss et al. |
| 4,817,166 A | 3/1989 | Gonzalez et al. |
| 4,825,263 A | 4/1989 | Desjardins et al. |
| 5,039,459 A | 8/1991 | Kindt-Larsen et al. |
| 5,066,120 A | 11/1991 | Bertrand |
| 5,080,839 A | 1/1992 | Kindt-Larsen |
| 5,081,685 A | 1/1992 | Jones, III et al. |
| 5,091,963 A | 2/1992 | Litt et al. |
| 5,094,609 A | 3/1992 | Kindt-Larsen |
| 5,123,735 A | 6/1992 | Hegarty |
| 5,164,462 A | 11/1992 | Yang |
| 5,249,029 A | 9/1993 | Sommer et al. |
| 5,260,576 A | 11/1993 | Sommer, Jr. et al. |
| 5,268,735 A | 12/1993 | Hayashi |
| 5,399,692 A | 3/1995 | Hung et al. |
| 5,466,768 A | 11/1995 | Yang |
| 5,500,024 A | 3/1996 | Hung et al. |
| 5,500,732 A | 3/1996 | Ebel et al. |
| 5,528,878 A | 6/1996 | Edwards et al. |
| 5,568,715 A | 10/1996 | Ebel et al. |
| 5,574,554 A | 11/1996 | Su et al. |
| 5,578,331 A | 11/1996 | Martin et al. |
| 5,623,816 A * | 4/1997 | Edwards et al. ............... 53/478 |
| 5,626,000 A | 5/1997 | Edwards et al. |
| 5,633,504 A | 5/1997 | Collins et al. |
| 5,640,464 A | 6/1997 | Ebel et al. |
| 5,649,410 A | 7/1997 | Martin et al. |
| 5,675,962 A | 10/1997 | Martin et al. |
| 5,687,541 A | 11/1997 | Martin et al. |
| 5,706,634 A | 1/1998 | Edwards et al. |
| 5,745,230 A | 4/1998 | Edwards et al. |
| 5,749,205 A | 5/1998 | Edwards et al. |
| 5,812,254 A * | 9/1998 | Ebel et al. ................... 356/124 |
| 6,018,931 A | 2/2000 | Byram et al. |
| 6,020,445 A | 2/2000 | Vanderlaan et al. |
| 6,024,448 A | 2/2000 | Wu et al. |
| 6,031,059 A | 2/2000 | Vanderlaan et al. |
| 6,042,230 A | 3/2000 | Neadle et al. |
| 6,124,594 A | 9/2000 | Duggan et al. |
| 6,246,062 B1 | 6/2001 | Ross, III et al. |
| 6,548,818 B1 * | 4/2003 | Ross et al. ............... 250/461.1 |

* cited by examiner

MISSING LENS DETECTION SYSTEM AND METHOD

CROSS REFERENCE TO RELATED APPLICATION

This application is a divisional of U.S. application Ser. No. 09/420,569, filed Oct. 19, 1999 is now U.S. Pat. No. 6,548,818, which is a continuation-in-part of U.S. application Ser. No. 09/187,579, filed Nov. 5, 1998, now U.S. Pat. No. 6,246,062, having the same title and incorporated herein by reference.

FIELD OF THE INVENTION

The present invention relates generally to systems for detecting the presence and optionally the position of a product within a container or package, and more particularly, to an apparatus and method for verifying the presence in the container of an ophthalmic product such as a contact lens.

BACKGROUND OF THE INVENTION

Automated systems are used for producing ophthalmic lenses as disclosed in U.S. Pat. No. 5,080,839. These systems have achieved a very high degree of automation and enable lenses to be molded, removed from the molds, further processed and subsequently packaged, all without any direct human involvement. Even with highly automated systems, however, it has been necessary for each package to be checked visually by personnel to verify that the package contained a lens. These arrangements have increased manpower requirements and the associated labor costs. Automated loading of lenses without verifying an actual transfer of a contact lens into a package can result in more than two percent of processed packages being shipped without a lens. This is more than ten times the average rate found on one production line which uses manual loading of lenses.

In one prior art system disclosed in U.S. Pat. No. 5,568,715, detection of a lens in a package is accomplished by backlighting the package with diffuse light and performing an optical inspection with a video camera. In this system, the package is illuminated from the bottom and a camera module disposed over the package takes a picture of the package. The image is processed by a computerized image processing system to determine whether the lens is missing from the package. While this approach works relatively well, it is expensive and software intensive.

U.S. Pat. No. 5,633,504 discloses a system and method for inspecting a hydrated contact lens by illuminating the lens and photographing with a camera the fluorescent light generated in the lens or in some portion of the receptacle and blocked by the lens. In the preferred method, the lens is provided with an ultraviolet absorbing medium. In one embodiment, light having certain wavelengths will induce fluorescence in the lens and cause the lens to appear as a bright area against a dark field. Defects in the lens appear darker than the surrounding areas. In another embodiment, a part of the lens holding receptacle or support is made to fluoresce by exposure to light having wavelengths outside of the range of wavelengths used by the camera. These wavelengths do not cause lens fluorescence such that defects appear as light areas within the lens.

Accordingly, there exists a need for a new type of lens detection system, which provides low cost detection with high accuracy. The detection system may be used as part of an automated detection system which includes a transport and ejector conveyor for ejecting any defective packages which the automated detection system determines are missing lenses in the packages.

SUMMARY OF THE INVENTION

It is a primary object of the present invention to provide a system and a method for verifying the presence and optionally the presence and position of an ophthalmic product disposed in the container by directing electromagnetic radiation at the product/container combination.

It is another object of the present invention to provide a system for verifying the presence or absence of an ophthalmic product disposed in the container which provides an accuracy of detection greater than 1 in 100,000.

It is still another object of the present invention to provide a system for verifying the presence or absence of an ophthalmic product disposed in a container which is economical to manufacture and use.

In accordance with the above objects and additional objects that will become apparent hereinafter, the present invention provides a system for determining the presence and optionally the position of an ophthalmic product such as a contact lens in a container. The lens will fluoresce, absorb or reflect, preferably absorb or reflect, most preferably absorb, electromagnetic radiation in a different amount than the container. This difference may be due to a media included in the lens, which reacts differently to electromagnetic energy in a specified wavelength range than does the container. The container includes a receptacle for the lens and preferably is at least partially constructed from a material which is substantially transparent to electromagnetic energy in the specified wavelength range. The detection system includes an apparatus for detecting the presence and optionally the position of an ophthalmic product in a container, comprising:

(a) a source of electromagnetic energy located relative to the container to direct electromagnetic energy at the container;

(b) a detector disposed relative to the container and the source to detect electromagnetic energy from the source which passes through or is reflected by the product and the container; and (c) a processor for determining the presence or position of the product in the container responsive to absorption, reflection or fluorescence of the electromagnetic energy by the product.

Another embodiment of the apparatus of the present invention for detecting the presence and optionally the position of an ophthalmic product in a container comprises:

(a) a source of electromagnetic energy located relative to the container to direct electromagnetic energy at the container;

(b) a reflective surface located such that the container is disposed between the source and the reflective surface;

(c) a detector disposed relative to the container and the source to detect electromagnetic energy from the source which is reflected by the product, the container and the reflective surface; and (d) a processor for determining the presence or position of the product in the container responsive to fluorescence, absorption or reflection of the electromagnetic energy by the product.

The present invention also provides a method for detecting the presence or presence and position of an ophthalmic product in a container, the product including a media which absorbs or reflects electromagnetic energy of a frequency in a specified range, the method comprising:

a) directing electromagnetic energy at the product and the container;

b) detecting the electromagnetic energy which passes through or is reflected by the product and the container; and c) processing the detected electromagnetic energy to determine the presence or position of the product in the container.

The present invention provides a relatively simple and economical system for determining the presence and optionally the position of an ophthalmic product in a container. It does not comprise a vision system, nor complicated software which does pixel-by-pixel analysis of an image, that is, image morphology.

BRIEF DESCRIPTION OF THE DRAWINGS

The present invention will now be described with particular reference to the accompanying drawings:

FIG. 5b is a cross-sectional view along axis A—A of the sensor head of FIG. 5a.

FIG. 6b is a cross-sectional view along axis A—A of the sensor head of FIG. 6a.

FIG. 6c is a cross-sectional view along axis B—B of the sensor head of FIG. 6a.

FIG. 6d is a cross-sectional view along axis C—C of the sensor head of FIG. 6a.

DETAILED DESCRIPTION OF THE PREFERRED EMBODIMENTS

The term "container" is used herein to mean a receptacle for the contact lens. Typically, the container will be a blister pack comprising a base (e.g. bowl) and a cover (e.g. lidstock). The cover can be for example a plastic cover which can be transparent or a plastic coated foil. The term "container" will be used herein to also refer to the base without a cover.

Figure 1:
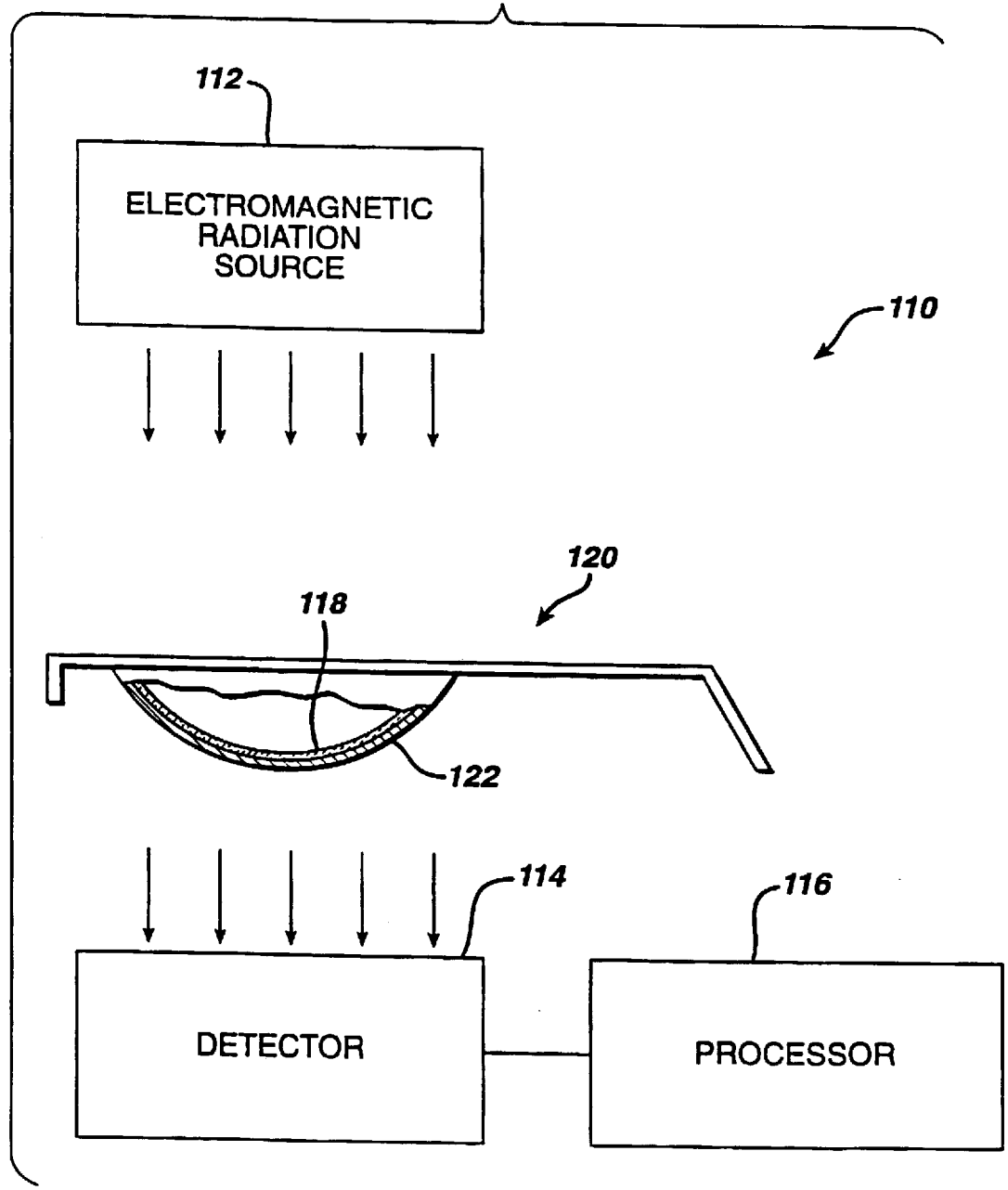
FIG. 1 is a schematic of a missing lens detection apparatus of the present invention showing the container between the radiation source and the detector.

A missing lens detection apparatus is shown in FIG. 1 and generally characterized by the reference numeral 110. The detection apparatus 110 comprises an electromagnetic radiation source 112, a detector 114, and a processor 116. The source 112 may be a broadband source, which produces ultraviolet light, visible light, and infrared light. For example, a visible light source, such as a Phillips light bulb P/NPL-S 9W/10, which will produce a portion of the electromagnetic radiation in the ultraviolet band. Alternatively, the source 112 may generate electromagnetic radiation in a narrow band, or the source may be used in combination with a wavelength filter to produce a narrow band. For example, the source may produce a narrow band of ultraviolet light (a wavelength or range of wavelengths within about 190 to 400 nanometers). In yet another embodiment, the source 112 may produce electromagnetic radiation in a selected group of ranges such as the ultraviolet and visible bands. The source 112 may emit a pulsed or constant electromagnetic radiation. A preferred source 112 emits pulses of ultraviolet light with a wavelength ranging from about 300 to about 400 nm and more preferably from about 300 to about 350 nm for a duration of about 100 $\mu$s per pulse. The source is preferably located away from the detector and the container and the electromagnetic energy is preferably carried to the container by a fiber optic, liquid light cable or light guide. The source 112 may be any source known in the art or commercially available which has the aforementioned features.

The detector 114 may be responsive to wavelengths of radiation in a particular range, or it may be responsive to broad bands and/or used in combination with a filter to detect a specified range of interest. The detector 114 may be a spectrometer, such as a photodiode or photosensor, or colorimeter. Preferably, the detector has a diameter of approximately 1 millimeter or thereabouts, and measures a total electromagnetic radiation sensed over the area of the detector. The detector 114 may be any detector known in the art commercially available which has the aforementioned features. Preferably, the detector 114 detects light having a wavelength from about 300 to about 400 nm and more preferably from about 300 to about 350 nm. For the embodiment shown in FIG. 1, an exemplary detector 114 is Part No. U.S. 365 HFI-010.00, available from Electronic Instrumentation Technology Inc., in Sterling Va. The EIT detector has a sensitivity for radiation having a wavelength of 365 nanometers, plus or minus about 20 nanometers, because it uses a bandpass filter arrangement to attenuate and limit the radiation to a narrow band width.

The apparatus may further comprise one or more additional electromagnetic sources and/or detectors. The inclusion of additional detectors typically improves the accuracy and precision of the missing lens detection system of the present invention.

In accordance with the invention, several source and detector frequency range combinations are possible. For example, a source 112 which produces electromagnetic energy in a broad band can be used with a detector 114 adapted to sense for a limited range. Alternatively, the source 112 can produce a limited range of wavelengths. Furthermore, both the source 112 and detector 114 can operate in the same band.

The detector 114 communicates with a processor 116, e.g. digital signal processor to provide an indication of the presence and optionally the position of an ophthalmic product 118, e.g., a lens, in a carrier or container 120. Preferably, the system is calibrated so that the ratio of the energy detected when the lens 118 is absent from the container 120 to the energy detected when the lens 118 is present in the container 120 is at least 1.1:1. More preferably, this ratio is at least 1.5:1 and most preferably greater than 2:1. The detector 114 is preferably sensitive to a limited number of wavelengths or range of wavelengths. For example, according to one embodiment of the invention, the detector 114 is sensitive to a bandwidth of about 200 nanometers or less, preferably less than about 50 nanometers, more preferably less than about 25 nanometers, and most preferably about 10 nm or less.

In one embodiment, the detector sends a single energy output to the processor where the output is compared to a standard. The electrical processing circuit is calibrated to operate with a range of limited voltages, for example, an 8V signal may be the highest voltage indicative of the absence of the lens 118 in the container, and a 3V signal indicative of the presence of the lens 118 in the container. The voltage signal could go to zero volts if the lens blocks all of the electromagnetic radiation, e.g. UV radiation which is detected by the detector. A predetermined limit can be established, such as when the sensed radiation results in a signal greater than 5V, to indicate the absence of the lens 118 from the container.

Similarly, the detector 114 can be calibrated to indicate whether the lens 118 is oriented properly in the container 120 or improperly disposed, for example, along the sides of the container receptacle or bowl described below. If lens 118 is not disposed in the proper orientation, the quantity of electromagnetic energy which is transmitted (less the radiation absorbed) or reflected back to the detector 114 may be less than the threshold value which indicates when the lens 118 is properly positioned. This information is used by the processor or communicated to a controller to reject or accept a container.

The processor of this invention can be any type of general purpose processor known to a person of ordinary skill in the art or commercially available, preferably a digital signal processor. The preferred processor is an Intel X-86 programmed to classify the analog signal from the detectors. The classification of the analog signal can be accomplished by converting the analog signal to a digital signal and analyzing the digital signal by, for example, a voting classifier, and/or lookup table, or by comparing the digital signal to boundaries established by neural network algorithms. Theoretically, the processor could analyze the analog signal; however, this is not preferred.

Figure 2:
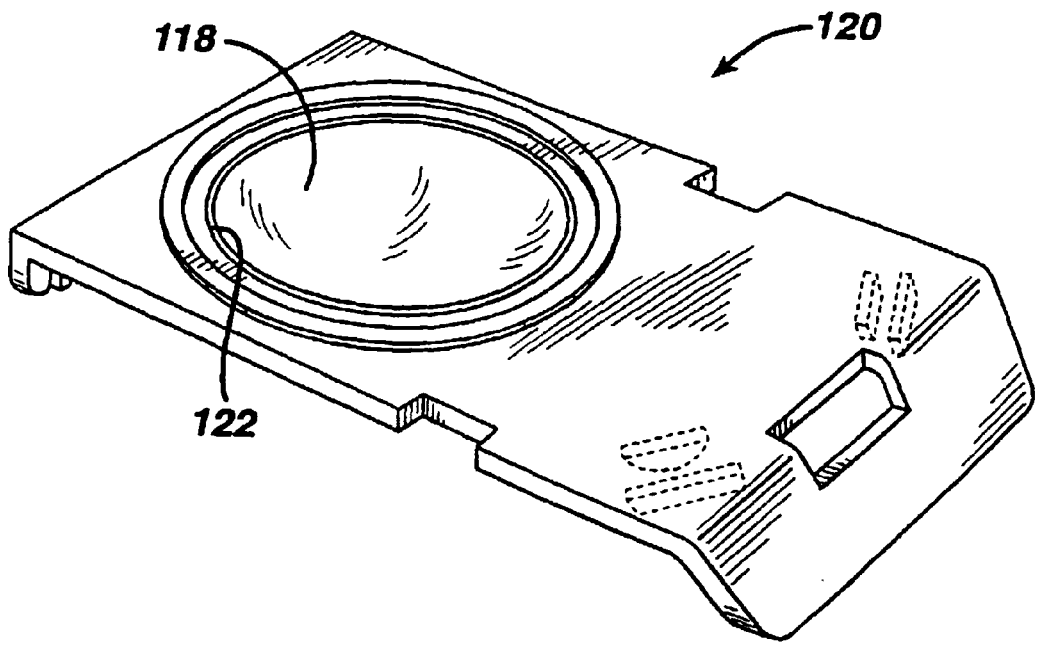
FIG. 2 is an isometric view of a container and lens disposed therein.
Figure 3:
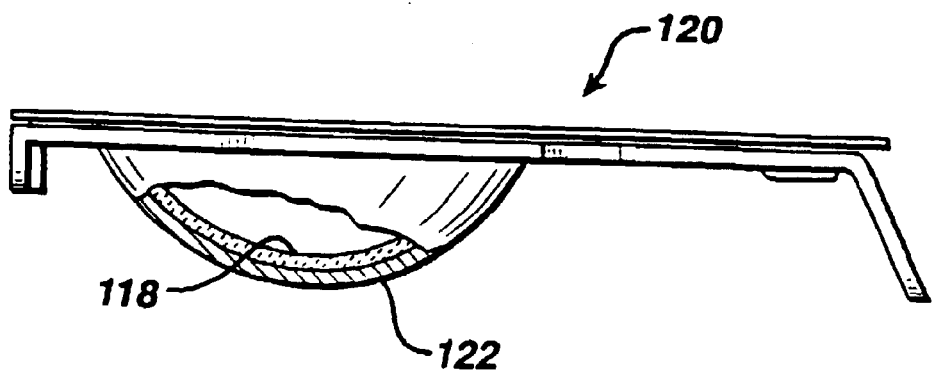
FIG. 3 is a side elevational view of the container and lens of FIG. 2.

In one embodiment, shown in FIG. 1, lens 118 is disposed within a receptacle or bowl 122 of the container 120 in a conventional manner as shown in FIGS. 2 and 3. The container 120 has a substantially planar top surface and the bowl is generally concave when viewed from the top of the container. The lens 118 is located in the bowl 122, and preferably, it is not immersed in liquid. Alternatively, the lens 118 can be fully submerged in a saline solution. The source 112 and detector 114 are disposed relative to the container 120 such that electromagnetic radiation is directed at the bowl 122 of the container 120 as shown in FIG. 1. In this embodiment, the container 120 has no lidstock. However, the container in this embodiment may have a transmissive lidstock.

The presence or position of the lens 118 within the bowl 122 can be determined as a function of the absorption of electromagnetic radiation passing through or reflecting from the lens 118 and container 120. The preferred contact lenses 118 used with the present invention contain an ultraviolet blocker which absorbs approximately 94% of UVA and UVB rays. An exemplary lens material is available under the tradename Etafilcon® with Norbloc® as the UV blocker. These lenses are commercially available under the tradename Surevue® and Acuvue® from Johnson & Johnson Vision Products, Inc., Jacksonville, Fla. Fabrication of a UV absorbing lens is known in the art as disclosed in, for example, U.S. Pat. No. 5,399,692, the disclosure of which is hereby incorporated by reference. Other patents which disclose contact lenses that absorb UV radiation include U.S. Pat. Nos. 4,390,676 and 4,528,311. UV radiation may also be absorbed by a UV photoinitiator.

The surrounding container material is selected so as to not appreciably absorb and block ultraviolet radiation to the same degree as the lens. Specifically, the plastic in the container 120 must not absorb and block the electromagnetic radiation in the range sensitive to detection by the detector 114 to the same degree as the lens 118. Exemplary plastic materials that may be used for the container 120 include, but are not limited to, polypropylene and polystyrene. Thus, the presence or position of the lens 118 within the container 120 can be determined by comparing the level of electromagnetic radiation received by the detector in the specified spectral range, for example, ultraviolet, with a known level for the container 120 alone. The processing circuitry 116 can provide a signal indicative of the presence or absence of the lens 118 based on the reduced electromagnetic radiation received by the detector.

In another embodiment, the source 112 can emit electromagnetic radiation in the infrared range. The presence of a lens 118 is indicated by a reduced level of infrared radiation at the detector 114 as compared to a baseline infrared level associated with an empty container 120. The container preferably includes a fluid such as an aqueous solution to facilitate transmitting infrared radiation from the container to the lens 118. The amount of aqueous solution in the container 120 can be just enough to wet the surfaces of the lens 118. The lens 118 is an infrared blocker (i.e. absorber) at certain wavelengths to which the detector 114 is sensitive. Testing has demonstrated good results using this method, although using UV radiation is presently preferred. It is also possible to utilize electromagnetic radiation in the visible spectral range. With this embodiment, a tinted lens 118 can be employed whereby the tinted lens absorbs and blocks electromagnetic energy in the visible spectrum to which the detector 114 is sensitive. Similarly, lens 118 may be more hygroscopic than the container 120. Therefore due to the presence of water in the lens, the lens may absorb or reflect the electromagnetic energy to a different degree than the container alone.

Figure 4A:
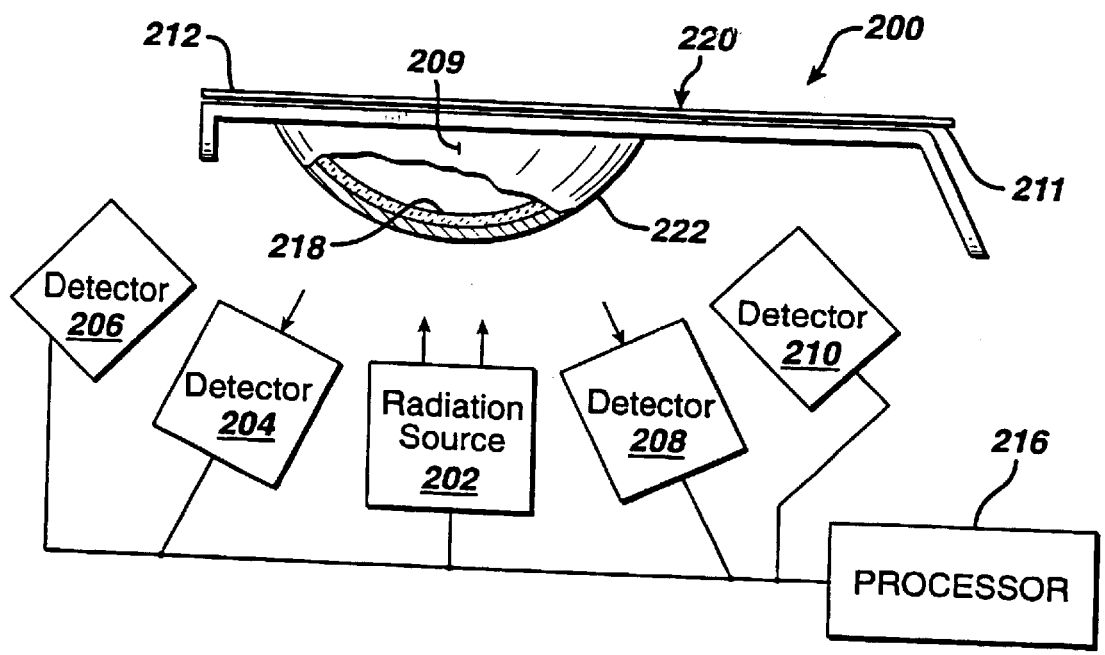
FIG. 4a is a schematic of another embodiment of a missing lens detection apparatus of the present invention, and a container.

Another embodiment of the missing lens detection apparatus of the present invention is shown in FIG. 4a. A missing detection apparatus 200 comprises an electromagnetic radiation source 202, preferably an ultraviolet source, and four detectors 204, 206, 208, and 210. The detectors 204, 206, 208, 210 preferably detect ultraviolet light and more preferably ultraviolet light having a wavelength of from about 300 to about 350 nm. There can be any number of detectors, preferably one to one hundred, more preferably one to twenty and most preferably one to ten. In the preferred embodiment, there are four detectors, e.g. photodiodes, used to detect the radiation from a single source to detect a contact lens in a container. There can be any number of sources, preferably one per container.

The electromagnetic radiation source 202 is oriented such that it is able to emit radiation toward a container 220 for containing an ophthalmic product, such as a lens 218. The container 220 has a lidstock 212 with a reflective surface 211 facing the inside of the container 220 and the electromagnetic source 202. Typically, the lidstock comprises foil, although it may comprise other reflective materials known in the art. The lidstock is preferably substantially flat. The detectors are located on the same side of the container as the source. The radiation is reflected off the lidstock.

Figure 4B:
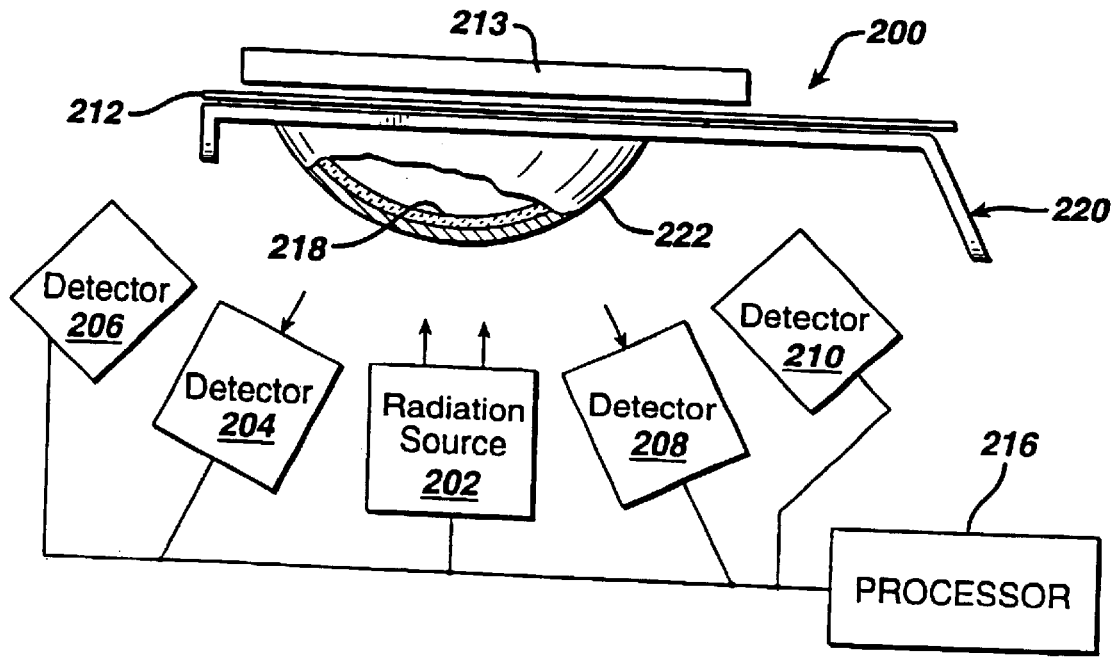
FIG. 4b is a schematic of yet another embodiment of a missing lens detection apparatus of the present invention, and a container.

Alternatively, the container may have a lidstock which is substantially transparent or no lidstock. The detectors can be placed opposite the electromagnetic source similar to the embodiment shown in FIG. 1 or a reflective surface, e.g. a plate 213 can be positioned opposite the electromagnetic source 202 with respect to the container 220 as shown in FIG. 4b. The reflective plate 213 performs the same function as the reflective surface of the lidstock 212. Alternatively, although not shown, the plate could be positioned under the bowl and the source could be positioned above the bowl.

The electromagnetic radiation is transmitted from the source 202 through the container 220 and reflected by the lidstock 212 or the reflective plate 213. If a lens 218 is present, the lens will absorb some of the source energy, and therefore, less energy will be reflected to the detectors 204, 206, 208, and 210. The detectors 204, 206, 208, and 210 provide a signal that correlates to the energy detected in the relevant frequency range that may be amplified, offset or otherwise normalized for later processing. The processing circuitry described above may be included in this embodiment.

The detectors 204, 206, 208, and 210 are preferably positioned around the source 202. More preferably, the detectors 204, 206, 208, and 210 are evenly spaced radially around the source 202 as shown in the missing lens detection sensor head 222 of FIGS. 5a and 5b. The sensor head 222 has a body 224 to which the source 202 and detectors 204–210 are mounted. Preferably, the detectors 204–210 are mounted such that they are aimed toward the center of the expected location of the lens. In the embodiment shown, the source and detectors are aimed toward the center of the top of the bowl of the container 201 labeled as 209 as shown in FIG. 4a.

Another embodiment of a sensor head 226 of the missing lens detection apparatus is shown in FIGS. 6a–6d. The sensor head 226 has a body 228 to which the detectors 204, 206, and 208 are mounted. The source 202 is offset from the center of the body 228 so that the source 202 is not centered under (or over) the lens in a container to be checked. The detectors 204, 206, and 208 are offset to the side of the apparatus 226 opposite the side the source 202 is located. Preferably, the detectors 204–208 are positioned along an arc. Also, the source 202 and detectors 204–208 are angled toward the expected location of the lens. Preferably, the source and detectors are aimed at the top center of the bowl labeled as 209 in FIG. 4a. Additional sources and detectors may be included in the apparatuses 222 and 226.

Referring to FIG. 4a, the detectors 204, 206, 208, and 210 communicate with a processor 216, e.g. a digital signal processing module (DSP) to provide an indication of the presence and optionally the position of the lens 218. Preferably, each detector transmits an amplified single voltage corresponding to the energy detected, which is converted to a discrete digital signal for further processing. The system may be calibrated as described above.

Figure 7:
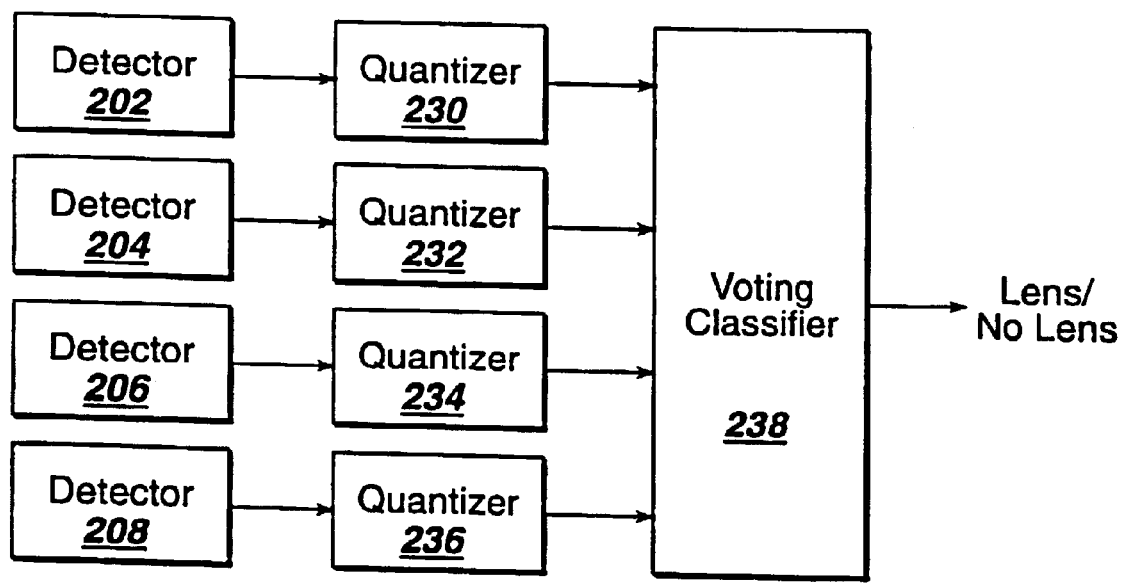
FIG. 7 is a block diagram of a processor for determining the presence of a lens from detector inputs.

FIG. 7 shows a block diagram of a portion of a missing lens detector apparatus including a voting classifier processor 238. As shown in FIG. 7, the detectors 204–210 provide an analog indication of the reflected power received which may be converted into digital representations based on predetermined voltage ranges by quantizers 230–236 or the like, respectively. A voting classifier 238 determines whether a lens 218 is present in the container 220 based on these digital representations. According to a preferred embodiment of the present invention, the voting classifier 238 determines the presence of the lens 218 with a lookup table containing predetermined values for each digital representation combination. This look-up table may optionally be generated during calibration by methods known in the art.

For example, if there are two possible digital representations, green and red indicating presence and absence of the lens 218, respectively, for the signals detected by each detector, there would 16 ($2^4$) possible combinations. According to one voting classifier scheme, if all four digital representations from the detectors 204–210 are red, the voting classifier 238 would determine that no lens 218 is present. For any other combination, the voting classifier 238 would determine that a lens 218 is present in the container 220.

Precision of the missing lens system may be increased by increasing the number of possible digital representations for each signal from each detector, i.e., by decreasing the size of the predetermined voltage ranges. For example, if there are three possible digital representations, green, yellow, and red indicating presence, possible presence, and absence of the lens 218, respectively, then there are 81 ($3^4$) possible combinations (as compared to only 16 combinations in the previous example). According to one voting classifier scheme, if three of the four digital representations are red and the fourth digital representation is yellow, the voting classifier 238 would determine that a lens 218 is not present. Also, if all four digital representations are red, the voting classifier 238 would determine that a lens 218 is not present. For any other combination, the voting classifier 238 would determine that a lens 218 is present in the container 220.

In the preferred embodiment, each photodiode (detector) is read by a twelve bit analogue to digital (A/D) converter which digitizes the signal into one of more than 100, more preferably more than 1000, and most preferably 4,096 discrete levels (referred to as counts). If the photodiodes detects no radiation, the count is 0. At maximum intensity, the count is 4,096. Therefore, the light intensity hitting the detector when a lens is not present is calibrated to achieve the top level of counts, in the preferred mode, an output of 4,096.

In the preferred embodiment, the apparatus for detecting the presence of a lens in a container comprises a sensor head comprising one radiation source and four detectors arranged around the source. The preferred sensor head looks like the apparatus shown in FIGS. 5a and 5b. The preferred apparatus has an array of six sensor heads to detect contact lenses in six containers simultaneously.

The processing can be accomplished using the above-described lookup table; however, in the preferred embodiment the processing is performed by a neural net algorithm processor which compares the signal level (counts) from the photodiodes of the detectors to ranges of counts in the algorithm for the presence or absence of a contact lens. The boundaries of the ranges of counts in the neural network are established by passing a teaching set comprising numerous, e.g. 10,000, containers having contact lenses in them through the system comprising the apparatus for detecting the contact lens in the container. This teaching set preferably includes samples representative of the production environment including extreme conditions, e.g. wrinkles of the reflective lidstock surface. The neural network algorithm is based on the perceptron model and establishes the decision boundaries when the outcomes are known for the teaching set. The neural network preferably makes no spatial connections between the detectors as would be necessary between pixels in an imaging focal plane array.

In the preferred embodiment, the electromagnetic source is a short arc zenon lamp made by Hamamatsu, which is a structured light source. The radiation from the source is concentrated at the expected position of the contact lens in the container, and as a result, the detectors are not flooded with stray light from the whole container. Further in the preferred embodiment, there is a filter placed on the light source which limits the electromagnetic energy to the wavelengths which are absorbed by the lens. In the preferred embodiment the light source is pulsed which heats the lens less and therefore avoids chemical changes or polymer damage in the lens by having low intensity light. In the preferred embodiment, the photodiodes are preferably silicon photodiodes, made by Advanced Photonix, United Detector Technology or Hamamatsu. The detectors preferably have low pass filters which only allow the radiation below 400 nm to pass through. The sensor heads comprising the sources and detectors were manufactured by Applied Computing Technology, Oakridge, Tenn. The processing and controls interface and electronics were also manufactured by Applied Computing Technology. Using a neural network algorithm processor increased the signal to noise ratio to 500:1.

Figure 8:
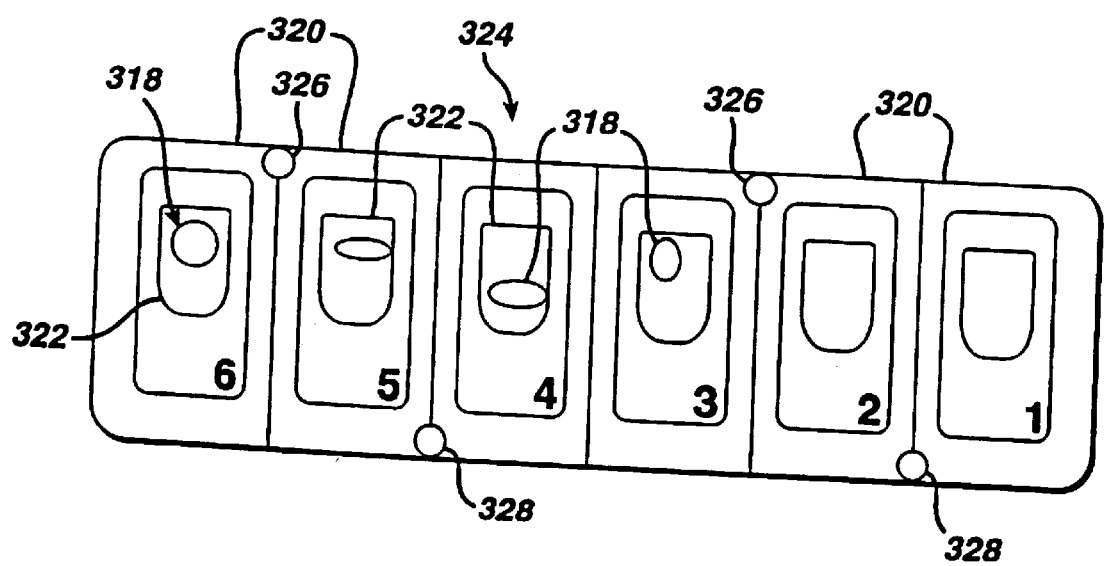
FIG. 8 is a top plan view schematic of an array of containers.

Referring now to FIG. 8, there is depicted a schematic top planar view of a blister container 324 comprising a linear array of six individual containers 320. Each container 320 is to be checked by the automated detection system to determine if each individual container has a lens 318 disposed in bowl 322. The containers 320 define first alignment lugs 326 depending from a first side of the container adjacent to and slightly spaced from the bowl 322, and second alignment lugs 328 depending from a second side of the container 320. If any lenses 318 are missing, the entire blister pack is rejected. Alternatively, the lenses 318 are contained in individual containers 320, at the time of detection, so that a missing lens 318 in a particular container 320 does not result in rejection of an entire group of containers 324.

Figure 5A:
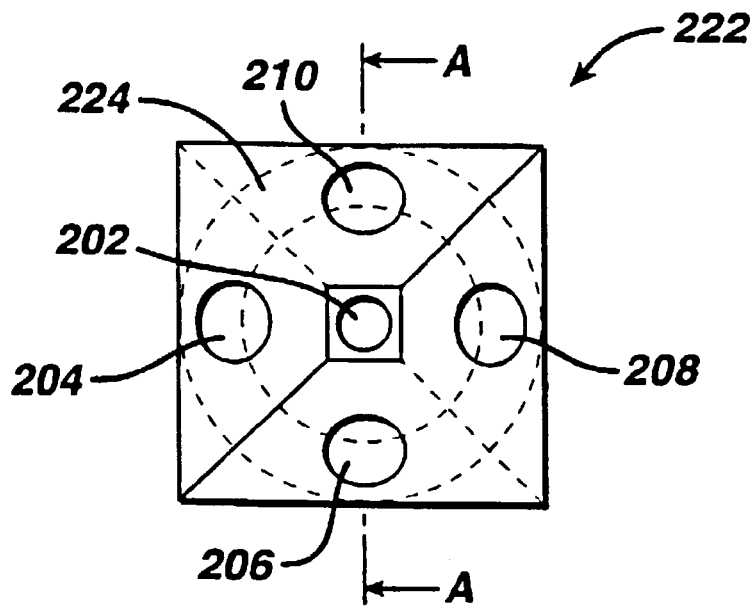
FIG. 5a is a top view schematic of a sensor head of the missing lens detection apparatus of the present invention.
Figure 5B:
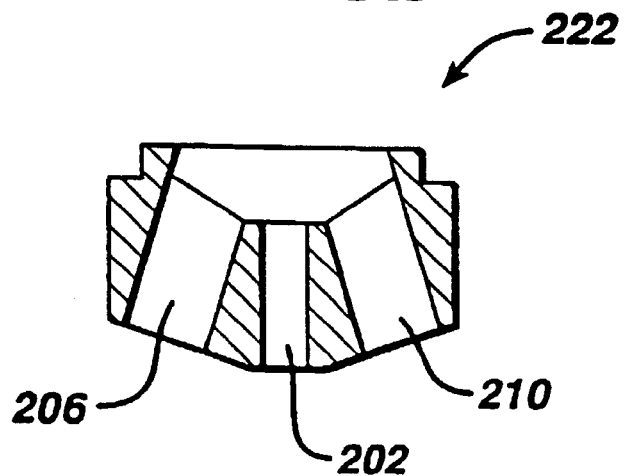
Figure 6A:
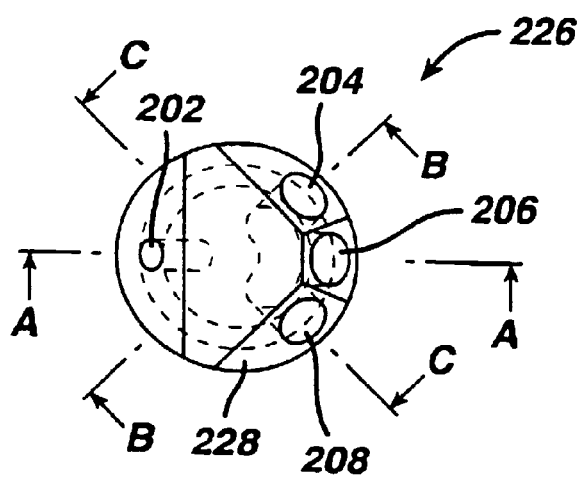
FIG. 6a is a top view schematic of another embodiment of a sensor head of the missing lens detection apparatus of the present invention.
Figure 6B:
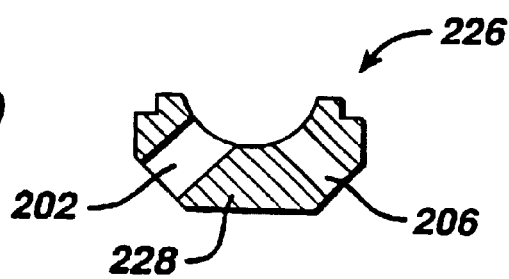
Figure 6C:
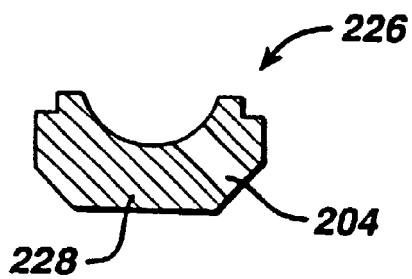
Figure 6D:
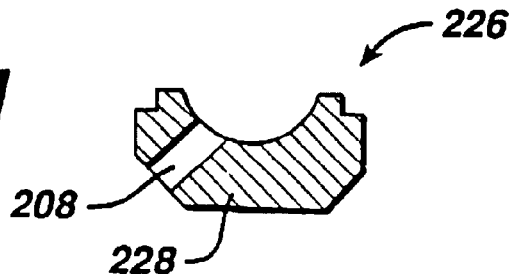
Figure 9:
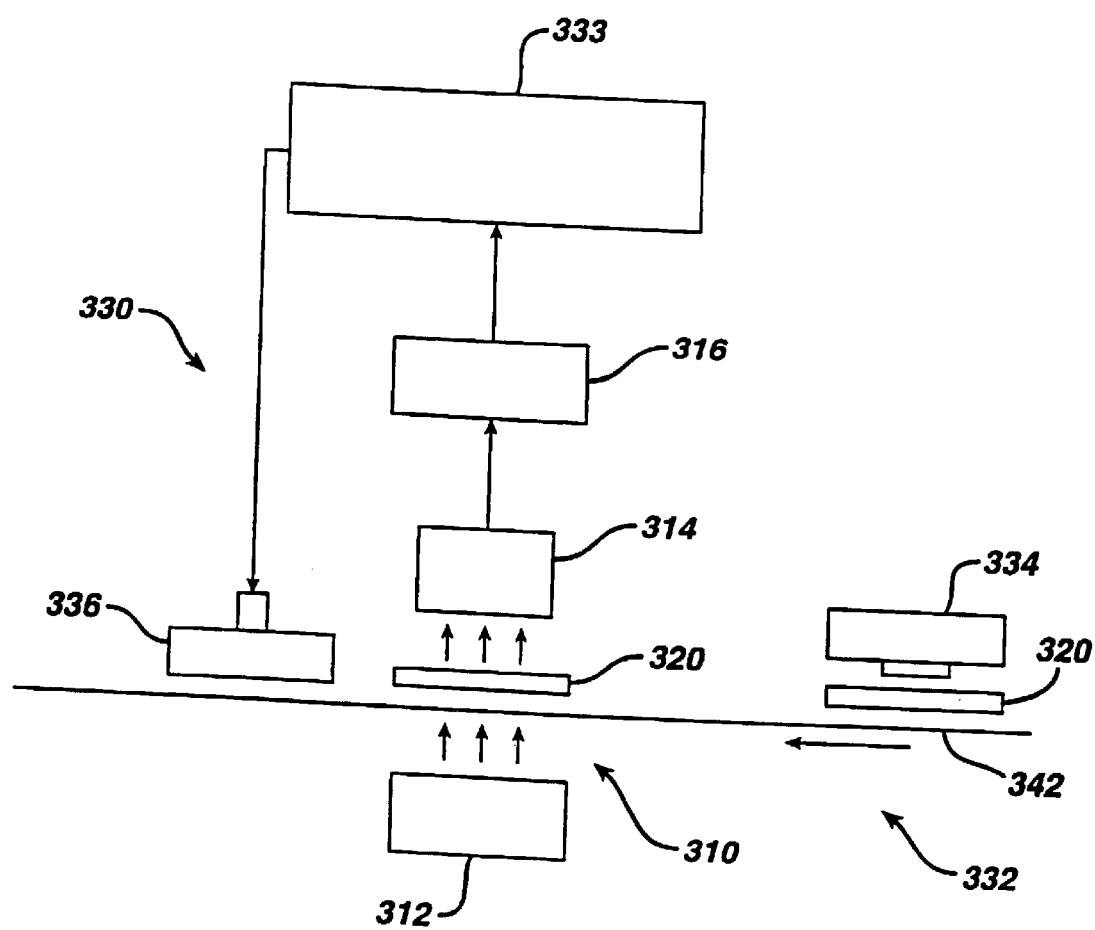
FIG. 9 is a schematic of an automated system for detecting a missing lens in accordance with the method of the present invention.

FIG. 9 is a schematic illustration of a lensload system 330 employing an automated detection system having a transport and ejector assembly. Details of a lensload system are disclosed in U.S. Pat. No. 5,568,715, the disclosure of which is hereby incorporated by reference. The system 330 generally comprises a transport subsystem 332, a missing lens detector 310, a processor 316, and a controller 333. The lenses (not shown) are transferred by a lens loading mechanism or assembly 334 that loads the lenses into the containers 320 and optionally seals the containers with a lidstock. The containers 320 are conveyed via a conveyor 342 in the direction of the arrow to the missing lens detector 310. The radiation from the electromagnetic radiation source 312 is directed as indicated by the arrows at and through the container 320 as shown. The radiation detector 314 measures the radiation which impinges on it, and the processing circuitry 316 which may be incorporated into the detector communicates the amount of radiation measured to the controller 333. When a reflective lidstock is attached to the container 320 or a reflective plate is opposite the source 312 with respect to the container 320, a missing lens apparatus as shown in FIG. 4a or 4b may be substituted for the missing lens detector 314. In the preferred embodiment, the container is sealed, the lidstock is reflective and the apparatus and sensor head shown in FIGS. 4a, 5a and 5b are used. The controller 333 which may be incorporated into the processor 316 is coupled to the reject mechanism 336. The reject mechanism 336, shown as a push-bar, under the control of the controller 333 removes those containers 320 which are missing lenses. Containers 320 that do not have a detected lens are pushed by a push bar 344 to another conveyor (not shown) which delivers them to a trash bin.

In this embodiment, detection is performed after hydration, and after transfer of the lens to the bowl of the final container. Lens detection may be performed before or after the addition of the saline solution and placement and attachment of the lidstock to the bowl of the container. The detection step is preferably after the inspection step, which uses a vision system and complicated software that occurs before the hydration step. More preferably, the detection step is performed after the lidstock is attached to the container to ensure that the final container contains the lens.

All patents, publications, applications, and test methods mentioned herein are incorporated by reference.

Many variations of the present invention will suggest themselves to those skilled in the art in light of the above detailed description. All such obvious variations are within the full intended scope of the appended claims.

What is claimed is:

1. An apparatus for detecting the presence or position of an ophthalmic product in a container, comprising:
   (a) a source of ultaviolet electromagnetic energy located relative to the container to direct electromagnetic energy at the container;
   (b) a detector disposed relative to the container and the source to detect electromagnetic energy from the source which passes through or is reflected by the product and the container; and
   (c) a processor for determining the presence or position of the product in the container responsive to fluorescence, absorption or reflection of the electromagnetic energy by the product.

2. An apparatus as defined in claim 1, wherein the product is a contact lens.

3. The apparatus according to claim 2, wherein the container comprises a reflective foil which reflects electromagnetic energy.

4. The apparatus according to claim 2, wherein the source emits pulsed electromagnetic energy having a wavelength in the ultraviolet range.

5. An apparatus as defined in claim 2, wherein the contact lens contains an ultraviolet absorbing media which absorbs electromagnetic energy in the ultraviolet range.

6. An apparatus as defined in claim 5, wherein said processor comprises a neural network algorithm.

7. An apparatus as defined in claim 2, wherein the lens is a hygroscopic lens.

8. An apparatus as defined in claim 2, wherein the lens includes a media which absorbs or reflects electromagnetic energy of a wavelength in a specified range, and the container includes a receptacle for the lens and is constructed from a material which absorbs or reflects the electromagnetic energy differently than the lens.

9. An apparatus as defined in claim 2, wherein said lens includes a media which absorbs or reflects electromagnetic energy having a wavelength in a specified range and said detector is sensitive to electromagnetic radiation in the specified range.

10. An apparatus as defined in claim 2, further comprising a plurality of sources and a plurality of detectors disposed relative to each other for detecting the presence or position of a contact lens in a container.

11. An apparatus as defined in claim 1, wherein said processor comprises a lookup table.

12. An apparatus as recited in claim 1, wherein said detector is a calorimeter.

13. An apparatus as recited in claim 1, wherein said detector is a spectrometer.

14. The apparatus recited in claim 13, further comprising a filter.

15. The apparatus according to claim 1, further comprising one to one hundred detectors.

16. The apparatus according to claim 1, further comprising one to twenty detectors.

17. A method for detecting the presence or position of an ophthalmic product in a container, the product including a media which fluoresces, absorbs or reflects the electromagnetic energy of a frequency in a specified range, the method comprising:

directing electromagnetic energy at the product and the container;

detecting the absence of or reduction in electromagnetic energy of a frequency in the ultraviolet range which passes through or is reflected by the product and the container; and processing the detected electromagnetic energy to determine the presence or position of the product in the container.

* * * * *